United States Patent
Wynne et al.

(10) Patent No.: US 8,138,351 B2
(45) Date of Patent: Mar. 20, 2012

(54) TREATMENT OF DUCHENNE MUSCULAR DYSTROPHY

(75) Inventors: Graham Michael Wynne, Abingdon (GB); Alexander Charles Weymouth-Wilson, Abingdon (GB); Robert Clarkson, Abingdon (GB); Renate Van Well, Abingdon (GB); Stephen Paul Wren, Abingdon (GB); Olivier De Moor, Abingdon (GB)

(73) Assignee: Summit Corporation PLC, Abingdon (GB)

( * ) Notice: Subject to any disclaimer, the term of this patent is extended or adjusted under 35 U.S.C. 154(b) by 151 days.

(21) Appl. No.: 12/599,970

(22) PCT Filed: Aug. 14, 2008

(86) PCT No.: PCT/EP2008/006719
§ 371 (c)(1),
(2), (4) Date: Jul. 1, 2010

(87) PCT Pub. No.: WO2009/021749
PCT Pub. Date: Feb. 19, 2009

(65) Prior Publication Data
US 2010/0267961 A1   Oct. 21, 2010

(30) Foreign Application Priority Data
Aug. 15, 2007   (GB) .................................. 0715937.9

(51) Int. Cl.
*C07D 263/57*   (2006.01)
(52) U.S. Cl. ....................................................... 548/217
(58) Field of Classification Search ........................ None
See application file for complete search history.

(56) References Cited

U.S. PATENT DOCUMENTS
4,110,246 A * 8/1978 Frischkorn et al. ...... 252/301.28
* cited by examiner

*Primary Examiner* — Kamal Saeed
(74) *Attorney, Agent, or Firm* — Heslin Rothenberg Farley & Mesiti P.C.

(57) ABSTRACT

Provided is a process for the preparation of 5-(ethylsulfonyl)-2-(naphthalen-2-yl) benzo[d] oxazole useful in the treatment of Duchenne muscular dystrophy.

10 Claims, 3 Drawing Sheets

CPD A – 5-amino-2-(5,6-dimethylbenzo[d]oxazol-2-yl)phenol
CPD B – 2-(4-(diethylamino)phenyl)-6-methyl-2H-benzo[d][1,2,3]triazol-5-amine

TREATMENT OF DUCHENNE MUSCULAR DYSTROPHY

RELATED APPLICATION

Priority is claimed herein to British application GB0715937.9, filed Aug. 15, 2007, entitled "TREATMENT OF DUCHENNE MUSCULAR DYSTROPHY." The above-referenced application is incorporated by reference herein in its entirety.

FIELD

Provided herein is a process for the preparation of a compound for the treatment of Duchenne muscular dystrophy.

BACKGROUND

Duchenne muscular dystrophy (DMD) is a common, genetic neuromuscular disease associated with the progressive deterioration of muscle function, first described over 150 years ago by the French neurologist, Duchenne de Boulogne, after whom the disease is named. DMD has been characterized as an X-linked recessive disorder that affects 1 in 3,500 males caused by mutations in the dystrophin gene. The gene is the largest in the human genome, encompassing 2.6 million base pairs of DNA and containing 79 exons. Approximately 60% of dystrophin mutations are large insertion or deletions that lead to frameshift errors downstream, whereas approximately 40% are point mutations or small frameshift rearrangements. The vast majority of DMD patients lack the dystrophin protein. Becker muscular dystrophy is a much milder form of DMD caused by reduction in the amount, or alteration in the size, of the dystrophin protein. The high incidence of DMD (1 in 10,000 sperm or eggs) means that genetic screening will never eliminate the disease, so an effective therapy is highly desirable.

A number of natural and engineered animal models of DMD exist, and provide a mainstay for preclinical studies (Allamand, V. & Campbell, K. P. Animal models for muscular dystrophy: valuable tools for the development of therapies. *Hum. Mol. Genet.* 9, 2459-2467 (2000). Although the mouse, cat and dog models all have mutations in the DMD gene and exhibit a biochemical dystrophinopathy similar to that seen in humans, they show surprising and considerable variation in terms of their phenotype. Like humans, the canine (Golden retriever muscular dystrophy and German short-haired pointer) models have a severe phenotype; these dogs typically die of cardiac failure. Dogs offer the best phenocopy for human disease, and are considered a high benchmark for preclinical studies. Unfortunately, breeding these animals is expensive and difficult, and the clinical time course can be variable among litters.

The mdx mouse is the most widely used model due to availability, short gestation time, time to mature and relatively low cost (Bulfield, G., Siller, W. G., Wight, P. A. & Moore, K. J. X chromosome-linked muscular dystrophy (mdx) in the mouse. *Proc. Natl. Acad. Sci. USA* 81, 1189-1192 (1984)).

Since the discovery of the DMD gene about 20 years ago, varying degrees of success in the treatment of DMD have been achieved in preclinical animal studies, some of which are being followed up in humans. Present therapeutic strategies can be broadly divided into three groups: first, gene therapy approaches; second, cell therapy; and last, pharmacological therapy. Gene- and cell-based therapies offer the fundamental advantage of obviating the need to separately correct secondary defects/pathology (for example, contractures), especially if initiated early in the course of the disease. Unfortunately, these approaches face a number of technical hurdles. Immunological responses against viral vectors, myoblasts and newly synthesized dystrophin have been reported, in addition to toxicity, lack of stable expression and difficulty in delivery.

Pharmacological approaches for the treatment of muscular dystrophy differ from gene- and cell-based approaches in not being designed to deliver either the missing gene and/or protein. In general, the pharmacological strategies use drugs/molecules in an attempt to improve the phenotype by means such as decreasing inflammation, improving calcium homeostasis and increasing muscle progenitor proliferation or commitment. These strategies offer the advantage that they are easy to deliver systemically and can circumvent many of the immunological and/or toxicity issues that are related to vectors and cell-based therapies. Although investigations with corticosteroids and sodium cromoglycate, to reduce inflammation, dantrolene to maintain calcium homeostasis and clenbuterol to increase muscle strength, have produced promising results none of these potential therapies has yet been shown to be effective in treating DMD.

An alternative pharmacological approach is upregulation therapy. Upregulation therapy is based on increasing the expression of alternative genes to replace a defective gene and is particularly beneficial when an immune response is mounted against a previously absent protein. Upregulation of utrophin, an autosomal paralogue of dystrophin has been proposed as a potential therapy for DMD (Perkins & Davies, Neuromuscul Disord, S1: S78-S89 (2002), Khurana & Davies, Nat Rev Drug Discov 2:379-390 (2003)). When utrophin is overexpressed in transgenic mdx mice it localizes to the sarcolemma of muscle cells and restores the components of the dystrophin-associated protein complex (DAPC), which prevents the dystrophic development and in turn leads to functional improvement of skeletal muscle. Adenoviral delivery of utrophin in the dog has been shown to prevent pathology. Commencement of increased utrophin expression shortly after birth in the mouse model can be effective and no toxicity is observed when utrophin is ubiquitously expressed, which is promising for the translation of this therapy to humans. Upregulation of endogenous utrophin to sufficient levels to decrease pathology might be achieved by the delivery of small diffusible compounds.

DESCRIPTION

It has been discovered that the compound of formula I has excellent properties for the treatment of Duchenne muscular dystrophy.

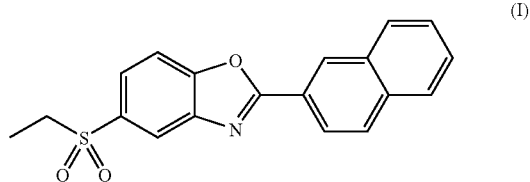

(I)

Accordingly, there is need for an efficient synthesis of the compound of formula (I): 5-(ethylsulfonyl)-2-(naphthalen-2-yl)benzo[d]oxazole.

Provided herein is a process for the preparation of the compound of formula (I)

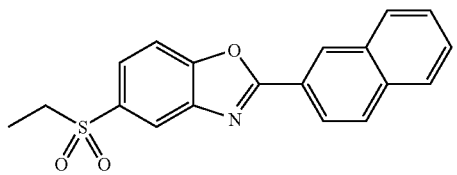

comprising a cyclisation of a compound of formula (II)

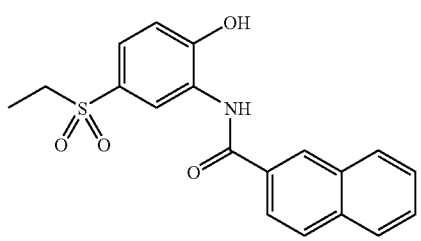

in the presence of an acid catalyst.

The instant disclosure will now be described with reference to the accompanying drawings in detail:

Figure 1:
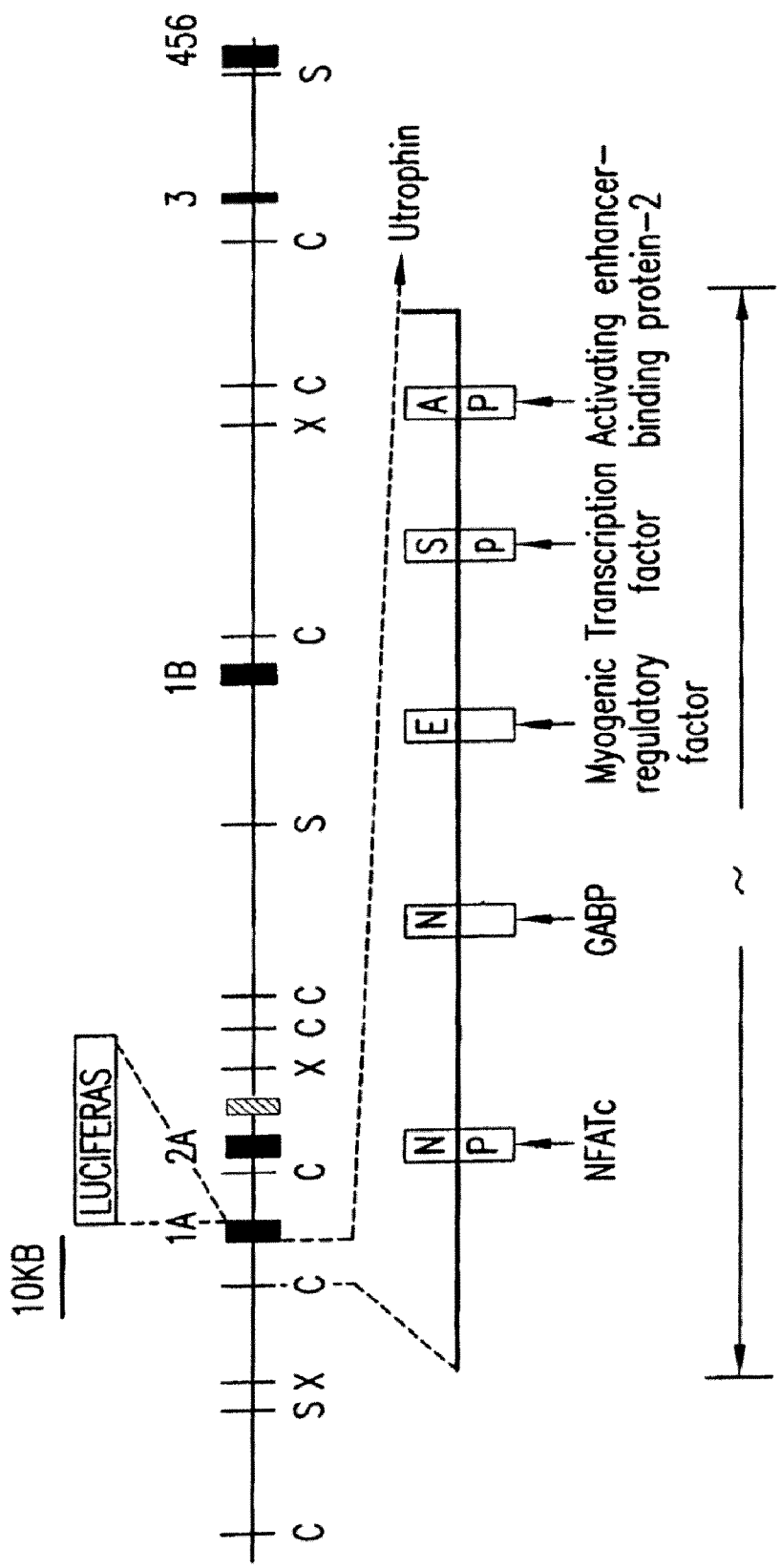
FIG. 1 shows a luciferase reporter assay (murine H2K cells).

There is broad scope for manipulation of the precise conditions of the reaction. All such manipulations are within the scope of the invention. Resources that would be of help to the skilled person when performing the invention include Vogel's Textbook of Practical Organic Chemistry, Fifth Edition, B. S. Furniss et al, Pearson Education Limited, 1988, which discusses general practical procedure. In addition, methods of synthesis are discussed in Comprehensive Heterocyclic Chemistry, Vol. 1 (Eds.: AR Katritzky, C W Rees), Pergamon Press, Oxford, 1984 and Comprehensive Heterocyclic Chemistry II: A Review of the Literature 1982-1995 The Structure, Reactions, Synthesis, and Uses of Heterocyclic Compounds, Alan R. Katritzky (Editor), Charles W. Rees (Editor), E. F. V. Scriven (Editor), Pergamon Pr, June 1996. Other general resources which would aid the skilled person include March's Advanced Organic Chemistry: Reactions, Mechanisms, and Structure, Wiley-Interscience; 5th edition (Jan. 15, 2001).

The reaction may be carried out at a temperature of from −10° C. to +170° C. Generally the reaction may be carried on at the reflux temperature of the solvent at normal pressure. It has been found that the reagents may be mixed whilst cold, without their being prior heated and before addition of solvent. Preparation in this manner did not adversely affect the reaction. This makes the physical processing easier and safer.

The reaction may be carried out in any suitable solvent that does not interfere with the reaction. Solvents that may be used include protic solvents such as acetic acid, formic acid, 1- and 2-propanol, 1- and 2-butanol, 3-Me-1-butanol, isobutanol, 1-pentanol, and aprotic solvents such as toluene, xylene (mixed), dioxane, 4-Me-2-pentanone, isobutyl acetate, n-propyl acetate and butyl acetate. In one embodiment, the solvent is xylenes (mixed).

In one embodiment, water produced as a by-product of the cyclisation is removed.

Methods of removing water from reactions are well known to the person skilled in the art. In one embodiment the water is removed by use of Dean-Stark apparatus. In the embodiment of the process when Dean-Stark apparatus is used it is preferred that the solvent has a boiling point greater than 100° C. It has been found that removal of water in this manner is beneficial to reaction rate and yield.

Any suitable acid catalyst may be used to catalyse the cyclisation, and many are known to the skilled person. Suitable catalysts include, but are not limited to p-toluenesulfonic acid and methanesulfonic acid.

In certain embodiments, rapid stirring is not essential. On a medium to large scale overhead stirring is sufficient, but it is not necessary to create a vortex.

The compound of formula (II) may be synthesised in any way. In one embodiment the compound of formula (II) is prepared by the reaction of an aminoalcohol of formula (III)

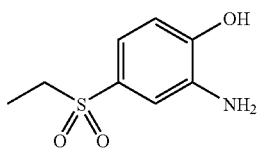

with an acyl derivative of formula (IV) wherein X represents a leaving group

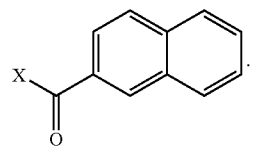

X represents any suitable leaving group. The skilled person is well aware of the range of suitable acyl derivatives available. However, in one embodiment, X represents halogen, wherein by halogen is meant F, Cl, Br or I. In another embodiment, X represents Cl.

The synthesis for the preparation of the compound of formula (II) may be carried out in any suitable solvent that does not interfere with the reaction. Solvents that may be used include protic solvents such as acetic acid, formic acid, 1- and 2-propanol, 1- and 2-butanol, 3-Me-1-butanol, isobutanol and 1-pentanol, and aprotic solvents such as toluene, xylene (mixed), dioxane, 4-Me-2-pentanone, isobutyl acetate, n-propyl acetate and butyl acetate. In one embodiment, the solvent is xylenes (mixed).

In one embodiment of the invention the compound of formula (II) is synthesised and purified in a separate step to the cyclisation step.

In another embodiment, a one-pot procedure is used, wherein the compound of formula (II) is synthesised and subsequently cyclised without intermediate purification of the compound of formula (II) or removal of solvent.

In one embodiment, an aminoalcohol of formula (III) and an acyl derivative of formula (IV) wherein X represents Cl are reacted in a solvent to give the compound of formula (II)

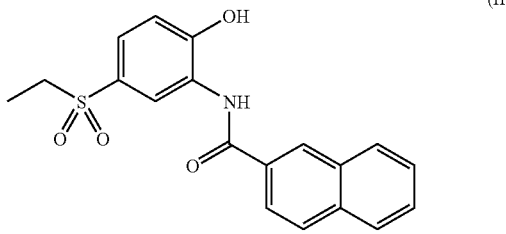

(II)

which is used in the process provided herein without intermediate purification or removal of the solvent.

During the reaction of the aminoalcohol and the acid chloride, HCl gas is liberated, which may be neutralised by a base. In one embodiment, the base is in an external trap. By external trap is meant the base is not present in the reaction mixture, and also that the HCl-base adduct is not produced in the reaction mixture. Use of an external trap simplifies purification, and minimises the risk of side-reactions catalysed by or involving the base. In one embodiment the liberated HCl gas may be neutralised by passing the exhaust gases from the reaction mixture through an alkali scrub, for example NaOH (aq). The skilled person is well aware of other scrubs that may be used to neutralise acidic exhaust gases from reactions.

In certain embodiments, the reaction of the amine with the acid chloride can be very quick and prolonged heating at this stage is not necessary. On a large scale (for example greater than one kilogram) gas evolution is quite rapid, and careful temperature control is necessary. For example, use can be made of jacketed reactors—the temperature can be increased slowly to a suitable level and then maintained at this temperature once HCl evolution begins. Once the HCl evolution is complete careful control need not be continued—the reaction may be monitored to observe completion by any suitable method, for example GCMS or TLC.

In another embodiment, X represents Cl, the reaction takes place in xylenes (mixed) under reflux, and the compound of formula (II) is used in the process provided herein without intermediate purification or removal of solvent, and in the cyclisation step methanesulfonic acid is used as the acid catalyst.

The product is isolated using conventional techniques. See for example Vogel's Textbook of Practical Organic Chemistry, Fifth Edition, B. S. Furniss et al, Pearson Education Limited, 1988, which discusses general purification techniques.

In one embodiment when the solvent is xylenes (mixed) the solution comprising the product is allowed to cool to about 90° C. and is then filtered. In certain embodiments, the temperature of the solution in the filtration step affects the yield and purity: the higher the temperature of the solution during filtration the greater the yield product and the lower the purity of the product.

Following filtration, the xylene (mixed) solution can be cooled causing the product to crystallise. The time taken for the product to crystallise is dependent on several factors—for example the concentration of the solution and the solvent used. However, in one embodiment, the reaction mixture is left for several hours.

After separation of the product by filtration optionally the product may be further purified by washing with a suitable solvent. Suitable solvents include, but are not limited to, MTBE, acetone and ethanol. In one embodiment, the solvent is methyl tert-butyl ether. Washing in this manner increases the purity of the product but may decrease the yield.

Further, the product may be recrystallised if necessary. Recrystallisation solvents that may be used include a mixed solvent comprising one of acetone, ethyl acetate, tetrahydrofuran and heptane in addition to an alcohol (for example ethanol). Recrystallization may also be performed in acetone alone.

The potential activity of the compound of formula I for use in the treatment of DMD may be demonstrated in the following predictive assay and screens.

1. Luciferase Reporter Assay (Murine H2k Cells)

The cell line used for the screen is an immortalized mdx mouse H2K cell line that has been stably transfected with a plasmid containing ≈5 kb fragment of the Utrophin A promoter including the first untranslated exon linked to a luciferase reporter gene (see FIG. 1).

Under conditions of low temperature and interferon containing media, the cells remain as myoblasts. These are plated into 96 well plates and cultured in the presence of compound for three days. The level of luciferase is then determined by cell lysis and reading of the light output from the expressed luciferase gene utilising a plate luminometer.

Figure 2:
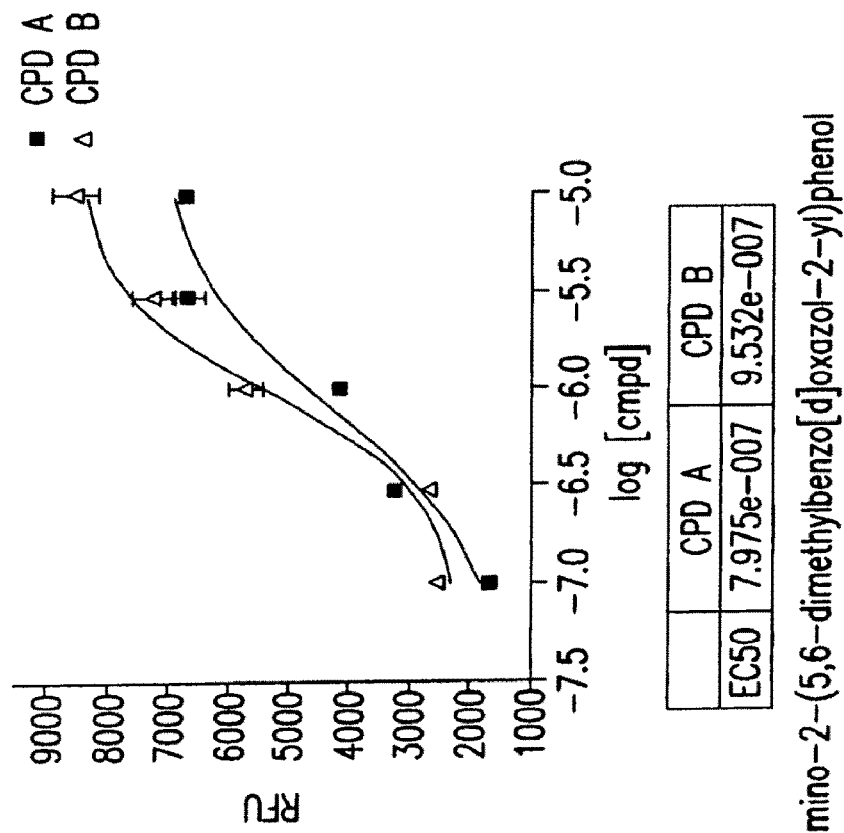
FIG. 2 shows a dose dependent luciferase induction.

Example of pharmacological dose response of compounds in the assay is shown in FIG. 2.

2. mdx Mouse

Data obtained from the ADMET data was prioritised and the compounds with the best in vitro luciferase activity and reasonable ADMET data were prioritised for testing in the mdx proof of concept study where the outcome was to identify whether any of the compounds had the ability to increase the levels of utrophin protein in dystrophin deficient muscle when compared to vehicle only dosed control animals.

There were two animals injected with 10 mg/kg of compound administered ip daily for 28 days plus age matched controls. Muscle samples were taken and processed for sectioning (to identify increases in sarcolemmal staining of utrophin) and Western blotting (to identify overall increases in utrophin levels).

Figure 3:
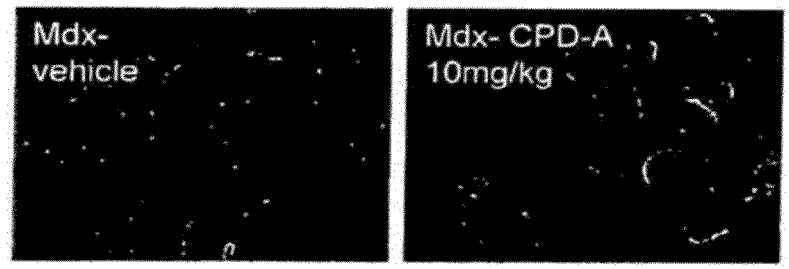
FIG. 3 shows an example of TA muscle sections stained with antibody specific for mouse utrophin.

FIG. 3 shows an example of TA muscle sections stained with antibody specific for mouse utrophin. Comparison to the mdx muscle only injected with vehicle shows an increase in the amount of sarcolemmal bound utrophin.

Figure 4:
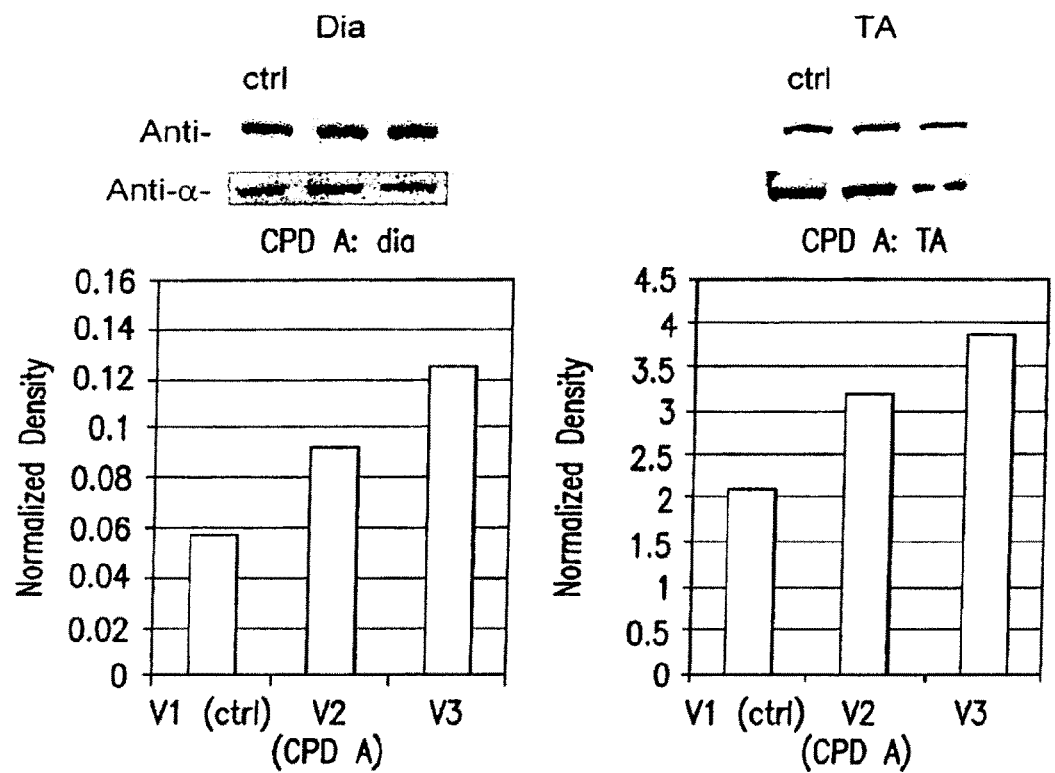
FIG. 4 shows that mice exposed to CPD-A (V2 and V3) showed increased levels of utrophin expression compared to control.

Muscles from the above treated mice were also excised and processed for Western blotting and stained with specific antibodies (see FIG. 4). Again using muscle dosed with CPD-A shows a significant increase in the overall levels of utrophin present in both the TA leg muscle and the diaphragm. Both mice exposed to CPD-A (V2 and V3) showed increased levels of utrophin expression compared to control.

Positive upregulation data from the first 28 day study were then repeated in a further two mouse 28 day study. A total of three different compounds have shown in duplicate the ability to increase the level of utrophin expression in the mdx mouse when delivered daily by ip for 28 days. This data demonstrates the ability of the compound when delivered ip causes a significant increase in the levels of utrophin found in the mdx muscle and therefore gives us the confidence that this approach will ameliorate the disease as all the published data to date demonstrates that any increase of utrophin levels over three fold has significant functional effects on dystrophin deficient muscle.

The H2K/mdx/Utro A Reporter Cell Line Maintenance

The H2K/mdx/Utro A reporter cell line was passaged twice a week until ≦30% confluent. The cells were grown at 33° C. in the presence of 10% $CO_2$.

To remove the myoblasts for platting, they were incubated with Trypsin/EDTA until the monolayer started to detach.

Growth Medium
DMEM Gibco 41966
20% FCS
1% Pen/Strep
1% glutamine
10 mls Chick embryo extract
Interferon (1276 905 Roche) Add fresh 10 µl/50 mls medium Luciferase Assay for 96 Well Plates The H2K/mdx/Utro A reporter cell line cells were plated out into 96 well plates (Falcon 353296, white opaque) at a density of approximately 5000 cells/well in 190 µl normal growth medium. The plates were then incubated at 33° C. in the presence of 10% $CO_2$ for 24 hrs.

Compounds were dosed by adding 10 µl of diluted compound to each well giving a final concentration of 10 µM. The plates were then incubated for a further 48 hrs.

Cells were then lysed in situ following the manufacture's protocols (Promega Steady-Glo Luciferase Assay System (E2520), then counted for 10 seconds using a plate luminometer (Victor1420).

Compound Storage

Compounds for screening were stored at −20° C. as 10 mM stocks in 100% DMSO until required.

Injection of mdx Mice with Compounds

Mdx from a breeding colony were selected for testing. Mice were injected daily with either vehicle or 10 mg/kg of compound using the intreperitoneal route (ip). Mice were weighed and compounds diluted in 5% DMSO, 0.1% tween in PBS.

Mice were sacrificed by cervical dislocation at desired time points, and muscles excised for analysis.

Muscle Analysis

Immunohistochemistry

Tissues for sectioning were dissected, immersed in OCT (Bright Cryo-M-Bed) and frozen on liquid nitrogen cooled isopentane. Unfixed 8 µM cryosections were cut on a Bright Cryostat, and stored at −80° C.

In readiness for staining, sections were blocked in 5% fetal calf serum in PBS for 30 mins. The primary antibodies were diluted in blocking reagent and incubated on sections for 1.5 hrs in a humid chamber then washed three times for 5 mins in PBS. Secondary antibodies were also diluted in blocking reagent, and incubated for 1 hr in the dark in a humid chamber. Finally sections were washed three times 5 mins in PBS and coverslips were mounted with hydromount. Slides were analysed using a Leica fluorescent microscope.

Results

Biological activity was assessed using the luciferase reporter assay in murine H2K cells, and is classified as follows:
+ Up to 200% relative to control
++ Between 201% and 300% relative to control
+++ Between 301% and 400% relative to control
++++ Above 401% relative to control

| 5-(ethylsulfonyl)-2-(naphthalen-2-yl)benzo[d]oxazole | +++ |

The invention will now be described in relation to the following example, which is intended to illustrate the invention and should not be construed as limiting.

EXAMPLE

The following materials were used:

| Material | Grade | Moles | Quantity |
|---|---|---|---|
| 2-Amino-4-(ethylsulfonyl)phenol | 97% | 4.72 mol | 948 g |
| 2-Naphthoyl chloride | 98% | 4.72 mol | 900 g |
| Methanesulfonic acid | 98% | 2.36 mol | 153 mL |
| Xylenes mixed | 96% | n/a | 6 L |
| Sodium hydroxide | — | 9.44 mol | 378 g |
| tert-Butyl methyl ether | 99% | — | 1.0 L |

Procedure:

A vessel was equipped with a retreat blade stirrer and downward pumping turbine, a five necked flange lid, seal and clamp, stirrer gland and overhead stirrer, thermometer pocket, Dean-Stark trap, dropping funnel and condenser. The water to the condenser was then switched on.

The sodium hydroxide and 0.80 L of water were then mixed (whilst cooling in an ice bath until all the sodium hydroxide has dissolved—caution exothermic). The resulting solution was then transferred to a scrubber appropriately attached to the vessel.

The 2-amino-4-(ethylsulfonyl)phenol and 2.00 L of xylenes (mixed) were then transferred to the vessel, and the reagents and solvent were stirred at 100 rpm.

Then, the 2-naphtholyl chloride was dissolved in 2.00 L of xylenes (mixed) and transferred into the vessel. The stirring rate was increased to 150 rpm.

The temperature of the solution was gradually increased to 100° C. over a period of not less than 30 mins, and then maintained at that level for 10 mins. (Caution: HCl gas is evolved during this process through the gas scrubber). The stirrer speed was then increased to 315 rpm and the temperature gradually increased over a period of 30 minutes until reflux (155° C.) at which level it was maintained for 90 mins. (Caution: HCl gas is evolved during this process through the gas scrubber).

The methanesulfonic acid was then added drop-wise over a period of 30 mins and relux was maintained until no further water was being collected in the Dean-Stark apparatus (approx 15 mins).

The heat was then removed and the pipe adapter from the Dean-Stark apparatus disconnected. The resulting solution was allowed to cool to 90° C., and then filtered using Whatman 1 filter paper.

The resulting solution was then left at ambient temperature for 18 h, after which time the product crystallised, and the product was separated by filtration using Whatman 1 filter paper. The product was then washed with 1×1.0 L of tert-butyl methyl ether (TBME)

The product was dried in a vacuum oven at 65° C. at a pressure of 10 mbar until constant weight was achieved (less than 0.5 g difference between consecutive measurements of mass which must be at least 1 h apart).

The product was obtained as a sandy-beige powder in a yield of 80%.

The product may be recrystallized by dissolving in refluxing acetone, cooling to −10° C. to −15° C., and filtering while cold.

Characterisation:
5-(Ethylsulfonyl)-2-(naphthalen-2-yl)benzo[d]oxazole
LCMS RT=6.94 min, MH+ 338.1;
$^1$H NMR (DMSO): 8.90 (1H, br), 8.34 (1H, d, J=1.4 Hz), 8.30 (1H, dd, J 8.6 1.7 Hz), 8.24-8.05 (4H, m), 7.99 (1H, dd, J 8.5 1.8 Hz), 7.73-7.64 (2H, m), 3.41 (2H, q, J=7.3 Hz), 1.15 (3H, t, J=7.3 Hz);
MP=160-161° C.

What is claimed is:

1. A process for the preparation of a compound of formula (I)

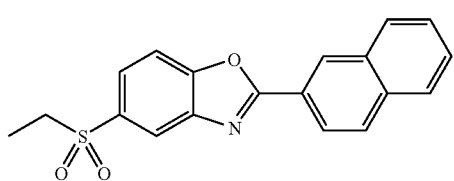

comprising a cyclisation of a compound of formula (II)

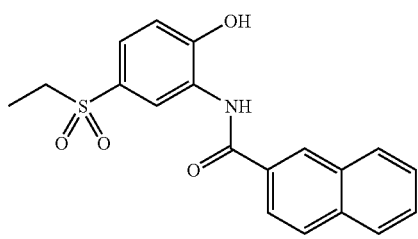

in the presence of an acid catalyst.

2. The process according to claim 1, wherein the acid catalyst is methanesulfonic acid or p-toluenesulfonic acid.

3. The process according to claim 1, wherein the process takes place in a solvent which is heated under reflux.

4. The process according to claim 3, wherein the solvent is a mixture of xylenes.

5. The process according to claim 1 wherein water produced as a by-product of the cyclisation is removed.

6. The process according to claim 5 wherein the water is removed by use of Dean-Stark apparatus.

7. The process according to claim 1, wherein the compound of formula (II) is synthesised in a solvent and subsequently cyclised without intermediate purification of the compound of formula (II) or removal of the solvent.

8. The process according to claim 1, wherein the compound of formula (II) is prepared by the reaction of an aminoalcohol of formula (III)

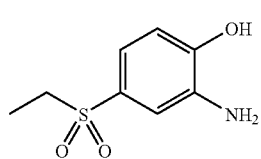

with an acyl derivative of formula (IV) wherein X represents a leaving group

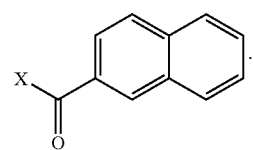

9. The process according to claim 8, wherein X represents halogen.

10. The process according to claim 8, wherein X represents Cl.

* * * * *